US006515175B2

(12) United States Patent
Mueller et al.

(10) Patent No.: US 6,515,175 B2
(45) Date of Patent: Feb. 4, 2003

(54) MONO-AND POLYAMIDES OF PERFLUOROALKYL-SUBSTITUTED UNSATURATED ACIDS

(75) Inventors: Karl F. Mueller, New York, NY (US); Michael Bochnik, Yonkers, NY (US); Marlon Haniff, West Orange, NJ (US); John Jennings, Yonkers, NY (US); Shobha Kantamneni, White Plains, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/978,156

(22) Filed: Oct. 15, 2001

(65) Prior Publication Data

US 2002/0068802 A1 Jun. 6, 2002

Related U.S. Application Data

(60) Provisional application No. 60/240,633, filed on Oct. 16, 2000, and provisional application No. 60/306,784, filed on Jul. 20, 2001.

(51) Int. Cl.⁷ ............... C07C 229/30; C07C 233/38; C07C 237/22; C07G 18/38
(52) U.S. Cl. ............... 562/565; 564/138; 564/142; 564/152; 564/153; 8/194; 8/128.1; 8/115.62; 427/430.1
(58) Field of Search ............... 562/565; 564/138, 564/142, 152, 153; 8/194, 128.1, 115.62; 427/430.1

(56) References Cited

U.S. PATENT DOCUMENTS

| | | | |
|---|---|---|---|
| 3,271,430 A | 9/1966 | Teumac | 260/404.5 |
| 3,567,500 A | 3/1971 | Moreau et al. | 117/139.5 |
| 3,754,026 A | 8/1973 | Beyleveld et al. | 260/534 |
| 3,769,307 A | 10/1973 | Moreau et al. | 260/404.5 |
| 4,606,973 A | 8/1986 | Schmidt et al. | 428/421 |
| 5,491,261 A | 2/1996 | Haniff et al. | 562/582 |
| 5,643,864 A | 7/1997 | Li et al. | 510/499 |

*Primary Examiner*—Brian J. Davis
(74) *Attorney, Agent, or Firm*—Kevin T. Mansfield

(57) ABSTRACT

Novel perfluoroalkyl-substituted mono-, di- and poly-amide compounds which are reaction products of a mono-, di- or polyamine of 60 to 2000 molecular weight with a perfluoroalkyl substituted unsaturated acid or its corresponding lower alkyl ester and optionally a non-fluorinated amino-reactive compound such as an acid, ester, anhydride, epichlorohydrin, isocyanate or urea, are useful as internally or externally applied paper sizes to impart oil and grease resistance to paper, and as oil proofing coatings on textiles, wood, masonry and the like, or as high-performance surface active agents.

30 Claims, No Drawings

MONO-AND POLYAMIDES OF PERFLUOROALKYL-SUBSTITUTED UNSATURATED ACIDS

This application claims the benefit under 35 U.S.C. 119(e) of U.S. Provisional Applications No. 60/240,633, filed Oct. 16, 2000 and No. 60/306,784, filed Jul. 20, 2001.

FIELD OF THE INVENTION

This invention relates to perfluoroalkyl-substituted mono-, di- and poly-amides derived from a perfluoroalkyl iodide, an unsaturated acid and a mono-, di-or polyamine. More particularly it relates to novel compounds which are the reaction products of a mono-, di- or polyamine of 60 to 2000 molecular weight with a perfluoroalkyl-substituted unsaturated acid or its corresponding lower alkyl ester and optionally a non-fluorinated amino-reactive compound such as an acid, ester, anhydride, epichlorohydrin, isocyanate or urea. These $R_F$-amides are useful as internally or externally applied paper sizes to impart oil and grease resistance to paper, and as oil proofing coatings on textiles, wood, masonry and the like, or as high-performance surface active agents.

BACKGROUND OF THE INVENTION

The use of perfluoroalkyl-substituted polymers to impart oil and water repellency to a variety of substrates, textiles especially, has long been known. The vast majority of these polymers are perfluoroalkyl-substituted methacrylate copolymers. Several patents also describe $R_F$-substituted polyurethanes, where $R_F$ stands for a perfluoroalkyl moiety. Polyamide-amino polymers derived from polyethyleneimine by reaction with esters of perfluoroalkyl-substituted carboxylic acids are described in U.S. Pat. Nos. 3,769,307 and 3,567,500. These polymers contain a mixture of $R_F$-substituted amide and secondary amino groups. These polymers are used to impart oleophobicity yet hydrophlilicity to textile substrates. Di-$R_F$ amido monocarboxylic acids prepared from 1 equivalent of diethylenetriamine, 2 equivalents of an $R_F$-acid and 1 equivalent of an anhydride are taught for use as textile finishes in U.S. Pat. No. 3,754,026. Similar $R_F$-amide-substituted polyethyleneimines useful as chemically resistant surfactants are described in U.S. Pat. No. 3,271,430. They are obtained by reaction of a perfluorinated alkanoic acid with a large excess of ethyleneimine. Reaction products of $R_F$-substituted acids with polymers bearing pendent primary amino groups attached to a carbon-carbon backbone by a linking group are claimed in U.S. Pat. No. 4,606,973 as low surface energy coatings on flat substrates.

U.S. Pat. No. 5,643,864 describes the synthesis of anionic surfactants by reaction of, for example, triethylenetetramine with first, two equivalents of a long-chain carboxylic acid, and secondly with chloroacetic acid. $R_F$-substituted acids are claimed as reactants but not described.

U.S. Pat. No. 5,750,043 and U.S. patent application Ser. No. 09/234,251 now U.S. Pat. No. 6,156,222 describe water-soluble $R_F$-substituted carboxylic acids that are amides of polyamines of 100 to 100,000 molecular weight which are used as foam stabilizers for aqueous fire fighting foams It has now been discovered that unsaturated alkenoic acids, preferably ωperfluoroalkyl substituted 10-undecenoic acid and tetrahydrophthalic acid, can be converted by reaction with a large variety of amines into mono-, di- and polyamides, which can be further reacted with non-fluorinated amino-reactive compounds such as acids, acid chlorides, esters, anhydrides, epichlorohydrin, isocyanates or urea to form monomeric and polymeric amides, amino-ethers, and ureas which are uniquely suitable—depending on their specific structure—as specialty surfactants or as oil and water repellents when applied to paper, textiles, wood, glass or masonry.

Perfluoroalkyl substituents which are attached to a long-chain hydrocarbon moiety, such as an undecenoic group, exhibit improved surface activity and improved effectiveness as oil repellents, possibly because such long-chain hydrocarbyl groups, by their inter-chain interactions, aid in the orientation of the very poorly interacting $R_F$-groups.

ω-Perfluoroalkyl-substituted 10-undecenoic acid and its use as an oil repellent paper size is disclosed in U.S. Pat. No. 5,491,261. Due to its relatively low molecular weight, this compound however shows substantial weight loss at the temperatures required for many paper product applications. This shortcoming has been overcome with the amide compounds of the present invention, which incorporate hydrogen-bonding amide groups and preferably contain more than one perfluoroalkyl-substituted undecenoic group.

DETAILED DISCLOSURE

The compounds of the present invention are mono-, di- or polyamides of the formulae

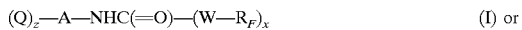  (I) or

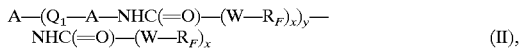  (II), wherein

A is the hydrocarbon residue of an aliphatic, cycloaliphatic or aromatic mono-, di- or polyamine of 60 to 2000 molecular weight, which is optionally substituted by hydroxy- and/or carboxyl groups and whose carbon chain is optionally interrupted by one or more ether, amide or amino groups, which amino groups are optionally substituted by substituents of the formula —Q— or —$Q_1$—, in which Q is a monovalent radical connected to a nitrogen atom of (A) and is derived from an acid, acid chloride or lower alkyl ester, an anhydride, a halogenated carboxylic acids an alkyl or alkenyl halide, an oxirane compound or chloroacetamide, and which is optionally substituted by one or more hydroxy-, tert. amino or carboxyl groups, or is optionally interrupted by one or more ether or thioether linkages, and optionally contains one or more unsaturated groups and can be substituted by an $R_F$ group, or is —P(=O)(OH)$_2$; —SO$_3$H; or —C(=O)—NH$_2$;

$Q_1$ is a difunctional linking group attached to the nitrogen atoms of two A groups and is derived from a diacid, diacid chloride or -lower alkyl ester, a dianhydride, a diisocyanate, epichlorohydrin, or is —C(=O)—, or is a trifunctional group derived from cyanuric acid, each $R_F$ is independently a monovalent perfluorinated alkyl or alkenyl, linear or branched organic radical having four to twenty fully fluorinated carbon atoms, W is —(CH$_2$)$_p$CH=CH— in which p is 1 to 20, or is a $C_6$-$C_{10}$cycloaliphatic hydrocarbyl group connecting an $R_F$ group to an amide carbonyl, z is zero to 50, y is zero to 50 and x is 1 to 10.

The compounds of the present invention preferably have a number average molecular weight of 1,000 to 10,000.

Preferably W is of the formula —(CH$_2$)$_p$CH=CH— in which p is 5 to 12 and is derived from a terminally unsaturated alkenoic acid, or is derived from tetrahydrophthalic anhydride or (methyl)-norbornene anhydride; R$_F$ is saturated and contains 4–14 carbon atoms, is fully fluorinated and contains at least one terminal perfluoromethyl group.

Most preferably W is of the formula —(CH$_2$)$_p$CH=CH— in which p is 8, and R$_F$ is saturated and contains 6–12 fully fluorinated carbon atoms.

When A is the hydrocarbon residue of an optionally substituted and/or interrupted monoamine, the amine is preferably an amino acid such as glycine, p-aminosulfonic acid or taurine, or an amino alcohol such as 2-hydroxyethanolamine or is a tert. amino-substituted amine residue of the formula —(CH$_2$)$_j$—N—(R$_1$)$_2$ wherein j is 2 to 6 and each R$_1$ is independently C$_1$-C$_4$alkyl, such as N,N-dimethylpropane-1,3-diamine. Especially preferred is a compound of the formula (II) wherein A is a tert. amino-substituted amine residue of the formula —(CH$_2$)$_j$—N— (R$_1$)$_2$ wherein j is 2 to 6 and each R$_1$ is independently C$_1$-C$_4$alkyl, W is of the formula —(CH$_2$)$_p$CH=CH— in which p is 8, and R$_F$ is saturated and contains 6–12 fully fluorinated carbon atoms.

When A is the hydrocarbon residue of an optionally substituted and/or interrupted diamine, the diamine is preferably of the formula H$_2$N—(CH$_2$)$_n$—NH$_2$ wherein n is 2–6, or is p-phenylenediamine, lysine, or a diamine of the formula
H$_2$N—(CH$_2$)$_3$—O—(CH$_2$—CH$_2$—O)$_m$—(CH$_2$—CHCH$_3$—O)$_l$—(CH$_2$)$_3$—NH$_2$, wherein m and l are independently 0 to 50 and m plus l is $\geq$1.

When A is the hydrocarbon residue of an optionally substituted and/or interrupted polyamine, the amine is preferably a polyalkyleneamine of the formula
H$_2$N—(CH$_2$CHR—NH)$_n$—CH$_2$CHR—NH$_2$, wherein n is 1 to 5 and R is hydrogen or methyl, or is aminoethylpiperazine, iminobispropylamine or N,N'-bis(3-aminopropyl)ethylenediamine, or is a polyethyleneimine of molecular weight 200 to 2,000 or polylysine.

Most preferably A is derived from a polyethyleneimine of molecular weight 200 to 1,000, diethylenetriamine, triethylenetetramine, N,N'-bis(3-aminopropyl)ethylenediamine, lysine or polylysine.

Preferred Q are of formula —C(=O)CH$_3$; —(CH$_2$)$_{1-3}$COOH; —C(=O)—CR=CH$_2$, wherein R is hydrogen or methyl; —CH$_2$CH=CH$_2$; —CH$_2$CH(OH)CH$_2$—O—CH$_2$CH=CH$_2$; —CH$_2$CH=CH—R$_F$ or —CH$_2$CH(OH)CH$_2$—O—CH$_2$—CH=CH—R$_F$, where R$_F$ is defined as above; —C(=O)—(CH$_2$)$_2$—COOH; —C(=O)—CH=CH—COOH; —C(=O)—C(=CH$_2$)—CH$_2$—COOH; —C(=O)—CH$_2$—C(=CH$_2$—COOH; —C(=O)(C$_6$H$_8$)—COOH; —C(=O)—(C$_7$H$_8$)—COOH; —C(=O)—(C$_8$H$_{10}$)—COOH; —C(=O)—(CH$_2$)$_8$CH=CH$_2$; —CH$_2$—CHOH—CH$_2$—O—(CH$_2$CHR—O)$_m$—R$_2$ where m is 1 to 50 and R$_2$ is hydrogen or C$_1$-C$_{12}$alkyl; —P(=O)(OH)$_2$; —SO$_3$H; or —CH$_2$CH$_2$N(CH$_3$)$_2$.

Most preferred are Q of formulae —C(=O)CH$_3$; —C(=O)—CH=CH$_2$; —CH$_2$—COOH; —C(=O)—(CH$_2$)$_2$—COOH and —C(=O)—(C$_6$H$_8$)—COOH.

Preferred Q$_1$ are of formula —(C=O)—HN—Z—NHC(=O)—, wherein Z is the diradical hydrocarbon residue of p- or m-toluene diisocyanate, isophorone diisocyanate, 3,3,4(3,4,4)-trimethylhexane-1,6-diisocyanate or hexane-1,6-diisocyanate; —C(=O)—; —CH$_2$—CHOH—CH$_2$— or —CH$_2$—CHOH—CH$_2$—O—(CH$_2$CH$_2$—O)$_m$—(CH$_2$CHCH$_3$—O)$_l$—CH$_2$—CHOH—CH$_2$—, wherein m and l are independently 0 to 50 and m plus l is $\geq$1; —C(=O)—C$_6$H$_4$(—COOH)$_2$—C(=O)—; or —C(=O)—CH$_2$C(=CH$_2$)—C(=O)— or —C(=O)—D—C(=O)—, wherein D is the hydrocarbon residue of an aliphatic or aromatic dicarboxylic acid having from 2 to 10 carbon atoms.

Most preferred Q$_1$ are of formula —CH$_2$—CHOH—CH$_2$—; —C(=O)—C$_6$H$_4$(—COOH)$_2$—C(=O)—; —C(=O)—CH$_2$CH$_2$—C(=O)— or —C(=O)HN—Z—NHC(=O)— wherein Z is the diradical residue of p- or m-toluene diisocyanate, isophorone diisocyanate, 3,3,4(3,4,4)-trimethylhexane-1,6-diisocyanate or hexane-1,6-diisocyanate.

The most preferred compounds of the formula (I) are of the formula

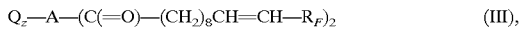
$$Q_z—A—(C(=O)—(CH_2)_8CH=CH—R_F)_2 \quad (III),$$

wherein
A is derived from diethylenetriamine, triethylenetetramine or N,N'-bis(3-aminopropyl)ethylene-diamine, Q is —C(=O)CH$_3$; —C(=O)—CH=CH$_2$; —CH$_2$—COOH; —C(=O)—(CH$_2$)$_2$—COOH or —C(=O)—(C$_6$H$_8$)—COOH, z is 1 or 2, and each R$_F$ is independently a monovalent perfluorinated linear alkyl radical having 6 to 14 fully fluorinated carbon atoms.

Most preferred compounds of the formula (II) are of formula

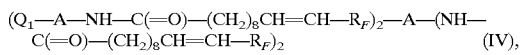
$$(Q_1—A—NH—C(=O)—(CH_2)_8CH=CH—R_F)_2—A—(NH—C(=O)—(CH_2)_8CH=CH—R_F)_2 \quad (IV),$$

wherein A is derived from diethylenetriamine and Q$_1$ is a difunctional radical of the formula —CH$_2$—CHOH—CH$_2$—; —C(=O)—CH$_2$CH$_2$—C(=O)—; —C(=O) —; —C(=O)—C$_6$H$_4$(—COOH)$_2$—C(=O)—, or —C(=O)—NH—Z—NH—C(=O)—, wherein Z is the diradical hydrocarbon residue of p- or m-toluene diisocyanate, isophorone diisocyanate, 3,3,4(3,4,4)-trimethylhexane-1,6-diisocyanate or hexane-1,6-diisocyanate and each R$_F$ is independently a monovalent perfluorinated linear alkyl radical having 6 to 14 fully fluorinated carbon atoms; most particularly a dimeric compound of the formula

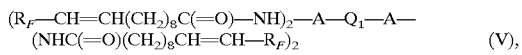
$$(R_F—CH=CH(CH_2)_8C(=O)—NH)_2—A—Q_1—A—(NHC(=O)(CH_2)_8CH=CH—R_F)_2 \quad (V),$$

wherein R$_F$, A and Q$_1$ are as defined above.

Also most preferred compounds of the formula (II) are of the formula

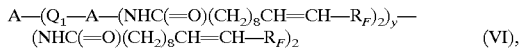
$$A—(Q_1—A—(NHC(=O)(CH_2)_8CH=CH—R_F)_2)_y—(NHC(=O)(CH_2)_8CH=CH—R_F)_2 \quad (VI),$$

wherein
y is 2 to 50, A is derived from triethylenetetramine or N'N-bis(3-aminopropyl)ethylenediamine and difunctional Q$_1$ is of the formula CH$_2$—CHOH—CH$_2$—, —C(=O)—CH$_2$CH$_2$—C(=O)—; —C(=O)—, —C(=O)—C$_6$H$_4$(—COOH)$_2$—C(=O)—, or —C(=O)—HN—Z—NH—C(=O)—, wherein Z is the diradical hydrocarbon residue of p- or m-toluene diisocyanate, isophorone diisocyanate, 3,3,4(3,4,4)-trimethylhexane-1,6-diisocyanate or hexane-1,6-diisocyanate, thus describing polymers of formula

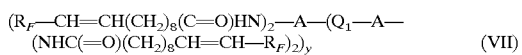
$$(R_F—CH=CH(CH_2)_8(C=O)HN)_2—A—(Q_1—A—(NHC(=O)(CH_2)_8CH=CH—R_F)_2)_y \quad (VII)$$

which are polyamides, polyureas or poly-tert. amines.

The novel $R_F$-products of the formula (I) or (II) can be synthesized in various ways. In one method, an aliphatic, cycloaliphatic or aromatic mono-, di- or polyamine is in a first step reacted with an $R_F$-acid, -ester or -anhydride at temperatures of 50 to 260° C., depending on the reactivity of the acid or ester, to form the corresponding $R_F$-amide intermediate which may contain unreacted secondary amino groups.

This amidification reaction is preferably carried out in bulk, but aprotic diluents can be present. Preferably a catalyst such as phosphoric acid is employed.

In a second step any remaining—mostly secondary—amino groups are reacted with an amino-reactive non-fluorinated compound. Useful reactants to convert remaining unreacted amino groups include anhydrides such as acetic anhydride, succinic and maleic anhydride, methendic and phthalic or tetrahydrophthalic anhydride; $C_1$-$C_8$carboxylic acids and their methyl esters; chloroacetic acid; alkyl halides such as allyl chloride; allyl glycidyl ether, urea and isocyanates.

If the reactants are difunctional reactants they can act as chain-extending agents. Typical of such compounds are diacids and their lower alkyl esters, such as glutaric acid and dimethylsuccinate or dimethyladipate, or anhydrides such as succinic and maleic anhydride, methendic and phthalic anhydride, also dianhydrides such as benzene- and benzophenone tetracarboxylic acid dianhydride; epichlorohydrin; urea, and aliphatic, cycloaliphatic and aromatic diisocyanates with 6 to 2 carbon atoms, such as 1,6-hexane diisocyanate, 2,2,3(2,3,3)-trimethylhexane-1,6-diisocyante, cyclohexane diisocyanate, isophorone diisocyanate and toluene diisocyanate. If the starting polyamine (P) is for example N,N'-bis-(3-aminopropyl) ethylenediamine, or a polyethyleneimine, the resulting reaction products are polyureas and polyamides.

In an alternate process, which is especially useful to prepare the most preferred compositions of this invention, a linear terminally-unsaturated monocarboxylic acid or its lower alkyl ester, or tetrahydrophthalic anhydride is first reacted with a polyamine, to form an oligoamide with residual secondary amino groups. Preferably this reaction is carried out without a solvent. Although, it is possible to use other linear terminally-unsaturated monocarboxylic acids, 10-undecenoic acid or its lower alkyl ester is preferred because $R_F$ substituents which are attached to the amino group through an intervening undecenoic group aid in the orientation of the $R_F$ groups and thereby improve their effectiveness as oil repellents.

In a second step, the remaining secondary amino groups are reacted with an amino-reactive non-fluorinated compound of the type described above to form a fully substituted intermediate. Finally, this ethylenically unsaturated intermediate is reacted with an $R_F$-iodide using a free radical generating mechanism as described for instance in U.S. Pat. Nos. 5,585,517 and 5,693,747; and in copending U.S. patent application Ser. No. 09/691,486.

Substituents —$CH_2CH=CH-R_F$ or —$CH_2CH(OH)CH_2$—O—$CH_2$—$CH=CH-R_F$, where $R_F$ is defined as above can be incorporated into the compound by reaction of amino groups with allyl chloride or allyl glycidyl ether at any convenient stage during the synthesis, but before the addition of the $R_F$-iodide.

Halogen-containing compounds, such as allyl chloride, mono-chloroacetic acid, chloromethyl benzene, xylylene dichloride, or methyl iodide or bromide can be further used for quaternization of tertiary amino groups. Tertiary amino groups are always present in polyethyleneimines, and also if allyl chloride or allyl glycidyl ether are used as co-reactants.

The final product mixture is then diluted, if desired, with sufficient deionized water to adjust the solids content to 15 to 50% and the fluorine content to 4 to 10%. Thus another aspect of the present invention is an essentially aqueous solution comprising 15 to 50% of a compound of the formula (I) or (II) as defined above.

The compounds of the formula (I) or (II) as defined above are useful as internally or externally applied paper sizes to impart oil and grease resistance to paper, and oil and grease resistant coatings on textiles, wood, masonry and the like, or as high-performance surface active agents.

When the compounds of the present invention are used as grease and oil repellent paper sizing agents, they are applied by methods known per se in amounts that are sufficient to deposit from 0.005 to 0.5% of organically bound fluorine by weight based on the dry paper weight. The compounds of the present invention can be applied externally in topical applications, for instance in a size press to the surface of paper or cardboard. They can also be applied internally, by adding them to an aqueous pulp together with other wet-end chemicals, as described for instance in U.S. Pat. No. 5,091,550, the disclosure of which is incorporated by reference, and more generally in W. F. Reynolds, "The Sizing of Paper", TAPPI Press, 1989. The compounds of the present invention are especially useful to impart oil and grease resistance to paper that is used for food packaging or contact applications.

Thus another aspect of the present invention is a method to impart oil and grease resistance to paper, which comprises incorporating an amount of a compound of the formula (I) or (II) as defined above that is effective to impart oil and grease resistance into the paper. Advantageously this method comprises treating paper or pulp with essentially aqueous solution comprising a sufficient amount of a compound of the formula (I) or (II) as defined above to deposit from 0.005 to 0.5% of organically bound fluorine by weight based on the dry weight of the paper onto the paper or pulp.

In addition to the fluorochemical, any of the conventional binders used in the paper industry—such as polymeric latex binders, carboxymethyl cellulose and polyvinyl alcohol—and sizing agents, such as ionic and nonionic starches such as ethoxylated and oxidized starches, and water sizing agents such as alkyl ketene dimer (AKD) or alkylsuccinic anhydride (ASA) can be employed.

The present invention further relates to a method to impart oil and grease resistance to a textile material, which comprises treating the textile material with an amount of a compound of the formula (I) or (II) as defined above that is effective to impart oil and grease resistance to the textile material.

The preferred amounts of the compounds of the present invention to treat the textile material are the same as for paper or pulp.

The present invention further relates to textile material or paper or pulp which contains from 0.005 to 0.5% by weight of a compound of the present invention incorporated therein.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

Unless otherwise noted, in the following non-limiting examples the perfluoroalkyl iodide ($R_F$I) used is Zonyl Tel A-N from DuPont, with a homologue distribution of 53.0% $C_8F_{17}I$, 30.6% $C_{10}F_{21}I$, 11.7% $C_{12}F_{25}I$, 3.6% $C_{14}F_{29}I$, and 1.0% $C_{16}F_{33}I$.

Examples 1–10 describe the synthesis of di- and tri-$R_F$ substituted N,N'-bis(3-aminopropyl)-ethylenediamine (APEDA) reaction products of the formula

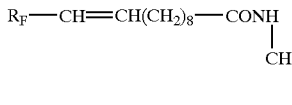 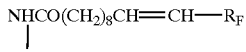

EXAMPLE 1
Diamide from 10-undecenoic Acid and N,N'-Bis(3-aminopropyl) ethylenediamine Into a 100 ml three-neck round bottom flask are placed 30.0 g 10-undecenoic acid (0.163 mol) and 0.6 g phosphoric acid (85%, 4.9 mmol). Then 14.7 g of N,N'-bis(3-aminopropyl)-ethylenediamine (0.085 mol) are added over 20 minutes to the acid with stirring, initially at 115° C. During the addition the temperature gradually increases to 162° C. and ice begins to collect in a preweighed Dean-Stark trap fitted with a dry ice condenser. The reaction temperature is gradually increased to 195° C. and is held there for 2 hours. The progress of the condensation is monitored by the amount of water collected and by gas chromatography. After two hours, 2.9 g distillate (97% of the theoretical weight of water) is collected and gas chromatography indicates that 5 mole % of the starting undecenoic acid is unreacted. The distillate contains less than 0.5% 10-undecenoic acid. A tan solid is obtained (33.6 g, 98.8%) with a m.p. of 105° C. Spectral data: $^1$H NMR (500 MHz, CDCl$_3$). δ: 4.92–5.10 (m, 4H, $H_{1a}$, and $H_{1b}$, $^3J_{trans}$=17.4 Hz, $^3J_{cis}$=10.9 Hz), 5.80 (m, 2H, $H_2$), 2.04 (q, 4H, $H_3$, $^3J$=6.98 Hz), 1.30–1.63 (m, 24H, $H_{4-9}$), 2.19 (t, 4H, $H_{10}$, $^3J$=6.90 Hz), 6.24 (t, 2H, $H_{11}$, $^3J$=5.6 Hz), 3.27 (q, 4H, $H_{12}$, $^3J$=6.98 Hz), 1.63 (quint., 4H, $H_{13}$, $^3J$=6.98 Hz).

EXAMPLE 2
N,N'-Bis(3-(11-perfluoroalkyl, 10-undecylenamido) propyl) ethylenediamine
Addition of Perfluoroalkyl Iodide 18.12 g (0.0358 mol) of the diamide from Example 1, 41.33 g (0.0678 mol) perfluoroalkyl iodide ($R_FI$) (DuPont's Zonyl Tel A-N), 15.95 g n-propanol, 36.13 g water, and 0.95 g sodium metabisulfite are added to a 300 ml three-necked, round-bottomed flask equipped with stirrer, condenser and nitrogen sparge inlet. The contents are heated to 70° C. and stirred. Then 0.52 g 2,2'-azobisisobutyronitrile (AIBN) are added. The contents are stirred at 70° C. for 4.0 hours. An opaque off-white paste is formed. GC analysis on a 30 m×0.53 mm SPB-5 polysiloxane column shows $R_FI$ conversion >98%. Then 11.28 g (0.141 mol) of a 50% sodium hydroxide solution are slowly charged to the stirred paste and the temperature is raised to 80° C. After 6 hours, iodide titration shows the dehydrohalogenation reaction to be complete.

The contents are allowed to settle and cool to 60° C. The top aqueous layer is removed and 5.0 g toluene are charged to aid phase separation in subsequent washes. The organic layer is washed three times with 40 ml water at 60° C. The organic layer is stripped of remaining solvents under vacuum at 70° C. and 44.98 g of a yellow-brown waxy material is obtained.

The product is dispersed into water in the following manner: to a rapidly stirred 63° C. solution of 82 g water, 0.5 g Brij 35 [polyoxyethylene(23) lauryl ether], 0.2 g Brij 98 [polyoxyethylene(20) oleyl ether], both from Aldrich Chem., and 1.0 g ammonium hydroxide (20%) are slowly added 16.0 g of the fluorochemical. After 1.5 hours, a creamy, off-white dispersion is obtained which can be used for performance evaluation.

EXAMPLE 3
N,N'-Bis(3-(11-perfluoroalkyl-10-undecylenamido)propyl) ethylene Diacetamide 12.3 g (0.024 mol) of the diamide from Example 1 are added to a 100 ml three-necked, round-bottomed flask equipped with stirrer, condenser and nitrogen sparge inlet, and heated to 70° C. while stirring. Then 6.39 g (0.063 mol) acetic anhydride are added over 15 minutes. After 1 hour, 27.37 g (0.0449 mol) $R_FI$, 10.66 g n-propanol, 24.80 g water, and 0.66 g sodium metabisulfite are added, followed by 0.96 g AIBN. The contents are stirred at 70° C. for 4.5 hours. An opaque off white paste is obtained. GC analysis on a 30 m×0.53 mm SPB-5 polysiloxane column shows $R_FI$ remaining to be <1.0% of the original charge. 14.02 g (0.175 mol) of a 50% sodium hydroxide solution is slowly charged to the stirred paste and the temperature is raised to 80° C. After 5 hours, iodide titration shows the reaction to be complete.

The contents are allowed to settle and cool to 60° C. The top aqueous layer is removed and 4.0 g toluene is charged to aid further washes. The organic layer is washed three times with 40 ml water at 60° C. The remaining paste is stripped of solvents under vacuum at 80° C. overnight and 32.60 g of a yellow waxy material is obtained.

EXAMPLE 4
N,N'-Bis(3-(11-perfluoroalkyl, 10-undecylenamido) propyl) ethylene Di-succinamide 11.71 g (0.023 mol) of the diamide from Example 1 are added to a 100 ml three-necked, round-bottomed flask equipped with stirrer, condenser and nitrogen sparge inlet and heated to 90° C. while stirring. Then 5.53 g (0.055 mol) succinic anhydride are added. After 2 hours, the anhydride flakes disappear and a reddish brown liquid is obtained. Then 26.01 g (0.0427 mol) $R_FI$, 11.21 g n-propanol, 25.62 g water and 0.65 g sodium metabisulfite are added, followed by 1.05 g AIBN. The contents are stirred at 70° C. for 4.0 hours. An opaque off-white paste is obtained. GC analysis on a 30 m×0.53 mm SPB-5 polysiloxane column shows remaining $R_FI$ to be <2.0% of the original charge. 14.15 g (0.177 mol) of a 50% sodium hydroxide solution is slowly charged to the stirred paste and the temperature is raised to 80° C. After 5 hours, iodide titration shows the reaction to be complete. 10.6 g acetic acid and 4.3 g toluene are slowly charged and, after 15 minutes of stirring, the contents are allowed to settle and cool to 60° C. The top aqueous layer is removed and the organic layer is washed two times with 40 ml water at 60° C. The paste is stripped of remaining solvents under vacuum at 80° C. overnight and 30.50 g of a brown waxy material is obtained.

Examples 5 and 6 describe di-$R_F$ substituted diethylenetriamine (DETA) reaction products of the formula

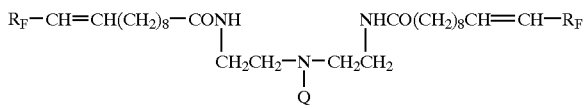

EXAMPLE 5
Diethylenetriamine-N,N"-bis-11-$R_F$-10-undecylenylamide-N'-succinamide 5a) Diethylenetriamine-N,N"-bis-10-undecylenylamide Into a 300 ml three-necked round bottom flask are placed 90.0 g undecenoic acid (0.488 mol) and 0.17 g phosphoric acid (85%, 14.6 mmol). Then 26.5 g of diethylenetriamine (0.251 mol) is slowly added with stirring to the acid, initially at 115° C. During the addition the temperature gradually increases to 165° C. and ice begins to collect into a pre-weighed Dean-Stark trap fitted with a dry ice condenser. Over 20 minutes, the temperature is increased to 195° C. and is held there for 1.5 hours to allow for complete reaction (theoretical weight of water is collected). A tan solid is obtained (108.1 g, 98.7%) with a m.p. of 74° C. and an Iodine Value of 54 (theoretical=59).

5b) Diethylenetriamine-N,N"-bis-10-undecylenylamide-N'-succinamide

Succinic anhydride (6.2 g, 0.0624 mol) is added to the product of Example 5a (25.0 g, 0.0594 mol amine) at 90° C. The melt is stirred at 90° C. for 1.5 hours; then gradually heated to 112° C. and held for an additional hour. GC analysis (using an external standard) indicates complete reaction of the anhydride.

5c) Diethylenetriamine-N,N"-bis-11-$R_F$-10-undecylenylamide-N'-succinamide

Following the procedure outlined in Example 2, 72.4 g (0.119 mol) perfluoroalkyl iodide are added to the product of Example 5b. The fluorochemical product is isolated to give 82 g of an amber solid that is dispersed into water in the following manner: to a rapidly stirred solution of 82 g water, 0.5 g Brij 35 [polyoxyethylene(23) lauryl ether], 0.2 g Brij 98 [polyoxyethylene(20) oleyl ether], both from Aldrich Chem., and 1.0 g ammonium hydroxide (20%) at 63° C. are slowly added 16.0 g of the fluorochemical. After 1.5 hours, a creamy, off-white dispersion is obtained which can be used for performance evaluation.

EXAMPLE 6
Diethylenetriamine-N,N"-bis-11-$R_F$-10-undecylenylamide-N'-urea

6a) A mixture of 25 g (0.0594 mol amine) product of Example 5a and 3.8 g (0.0624 mol) urea is melted together at 138° C. for 30 minutes; foaming occurs due to evolution of ammonia; then the melt is warmed to 140° C. with stirring and placed under vacuum (100 mm) for an additional hour to give 27.8 g (100%) diamido-urea.

6b) Following the procedure outlined in Example 2, 72.4 g (0.119 mol) perfluoroalkyl iodide are added to the product of Example 6a. The fluorochemical product is isolated to give 86.2 g of a yellow powder, which is emulsified in the following manner: 20 g of the fluorochemical are dissolved in 35 g isopropyl acetate at 70° C. Then a solution of 92 g water and 4.0 g Ethoquad 18/25 at 69° C. is slowly added to the isopropyl acetate solution with rapid stirring. Stirring is continued for an additional 40 minutes, at which time the mixture is passed twice through a high-pressure homogenizer. The organic solvent is removed under vacuum, resulting in a milky white, stable dispersion which can be used for performance evaluation.

EXAMPLE 7
Reaction Product of Lysine, 10-undecenoic Acid and $R_F$-iodide

7a) Reaction of Lysine with 10-undecenoic Acid

Into a 100 ml three-neck round bottom flask are placed 18.4 g 10-undecenoic acid (99.8 mmol) and 18.3 g L-lysine monohydrochloride (100 mmol). Then 4.1 g of crushed sodium hydroxide (98%, 100 mmol) is slowly added to the mixture with stirring at 110° C. After 10 minutes of stirring, 0.6 g phosphoric acid (85%, 5.2 mmol) is added. The temperature is increased to 200° C. and stirred for 5 hours. Ice begins to collect at 180° C. into a pre-weighed Dean-Stark trap fitted with a dry ice condenser. The progress of the condensation is monitored by the amount of water collected and by gas chromatography. After four hours, gas chromatography indicates that 4.5 mole % of the starting undecenoic acid is unreacted and 4.2 g water is collected. An amber solid is obtained in quantitative yield with an Iodine Value of 63.8. Anal. calcd. for $C_{17}H_{30}N_2O_2ClNa$: C, 57.81; H, 8.50; N, 7.93; Cl, 10.07. Found: C, 57.67, H, 8.09; N, 7.56; Cl, 10.17.

7b) Addition of $R_F$-iodide

Following the procedure outlined in Example 2, 60.8 g (0.0998 mol) perfluoroalkyl iodide are added to the product of Example 7a. The fluorochemical product is isolated to give 92 g of an amber solid that is homogenized in the following manner: with rapid stirring at 70° C., 20 g of the fluorochemical are slowly added to a solution of 11.8 g tripropylene glycol, 50 g water and 1.0 g Brij 98, with the pH adjusted to 8 with glacial acetic acid. The mixture is rapidly stirred for 1.5 hours, and then is passed three times through a high-pressure homogenizer to give a stable emulsion that will be used for performance evaluation.

EXAMPLE 8

The procedure of Example 7 is repeated, but using an approximately 2:1 molar ratio of 10-undecenoic acid (18.4 g, 0.0998 mol) to lysine (9.1 g, 0.05 mol), and adding $R_FI$ (60.8 g, 0.0998 mol), resulting in a bis-$R_F$-undecylenamido carboxylic acid.

EXAMPLE 9
N,N'-di-(11-perfluoroalkyl-10-undecylenyl Amide)-1,3-diaminopropane 9a) Reaction of 10-undecenoic Acid with 1,3-diaminopropane Into a 100 ml three-neck round bottom flask are placed 30.0 g 10-undecenoic acid (0.163 mol) and 0.6 g phosphoric acid (85%, 4.9 mmol). Then 6.3 g of 1,3-diaminopropane (0.085 mol) is slowly added to the acid with stirring, initially at 115° C. During the addition the temperature gradually increases to 162° C. and ice begins to collect into a pre-weighed Dean-Stark trap fitted with a dry ice condenser. The reaction temperature is gradually increased to 195° C. and is held there for 2 hours. The progress of the condensation is monitored by the amount of water collected and by gas chromatography. After two hours gas chromatography indicates that only 5 mole % of the starting undecenoic acid is unreacted and 2.9 g distillate (97% of the theoretical weight of water) is collected. The distillate contains less than 0.5% undecenoic acid. A tan solid is obtained (33.6 g, 98.8%) with a m.p. of 105° C. Spectral data: $^1$H NMR (500 MHz, CDCl$_3$). δ: 4.92–5.10 (m, 4H, H$_{1a}$, and H$_{1b}$, $^3$J$_{trans}$=17.4 Hz; $^3$J$_{cis}$=10.9 Hz), 5.80 (m, 2H, H$_2$), 2.04 (q, 4H, H$_3$, $^3$J=6.98 Hz), 1.30–1.63 (m, 24H, H$_{4-9}$), 2.19 (t, 4H, H$_{10}$, $^3$J=6.90 Hz), 6.24 (t, 2H, H$_{11}$, $^3$J=5.6 Hz), 3.27 (q, 4H, H$_{12}$, $^3$J=6.98 Hz), 1.63 (quint., 4H, H$_{13}$, $^3$J=6.98 Hz).

9b) R$_F$-iodide Addition

At 50° C., 1.0 g (5.2 mmol) sodium metabisulfite, and 0.4 g (2.0 mmol) 2,2-azobis (2-methyl-butyronitrile) (DuPont's VAZO-67) are added to a mixture of 10.6 g (51.7 mmol) of the reaction product of Example 8a, 30.0 g (49.6 mmol) perfluoroalkyl iodide (DuPont's Zonyl Tel A-N), 13.0 g 2-propanol and 6.0 g deionized water. The reaction temperature spontaneously increases to 77° C. The mixture is stirred for 2 hours, at which time less than 2 mole % of starting perfluoroalkyl iodide is unreacted based on gas chromatography analysis. 8.1 g KOH (45%) (72.4 mmol) are added to the di-R$_F$-iodohydrin. Then the reaction mixture is stirred at 70° C. for an additional 2.5 hours to allow for complete dehydroiodination (as ascertained by AgNO$_3$ titration). Then 2-propanol is azeotroped off under vacuum and the product mixture is poured into 300 ml ice water, sheared in a high speed blender, filtered and washed on a Buchner funnel; then dried at 50° C. in a vacuum oven to give 29.3 g (88.8%, m.p. 81–86° C.) of off-white powder. Spectral data: $^1$H NMR (500 MHz, CDCl$_3$). δ: 6.40, 6.12 (m, 2H, H$_1$, 80/20 trans/cis), 5.60, 5.49 (q, 2H, H$_2$, $^3$J=13.2 Hz), 2.12, 1.99 (m, 8H, H$_3$ and H$_{10}$), 1.30, 1.44, 1.64 (m, 24H, H$_{4-9}$), 6.18 (bt, 2H, H$_{11}$, $^3$J=5.7 Hz), 3.28 (q, 4H, H$_{12}$, $^3$J=6.9 Hz), 1.63 (m, 2H, H$_{13}$).

The fluorinated diamide is dispersed into water in the following manner: 5.7 g of the fluorochemical are added with stirring to an 80° C. solution of 3.7 g tripropylene glycol, 0.3 g Brij 98, 0.23 g NaOH (10%) and 15.3 g water. After 45 minutes of stirring, a stable dispersion is obtained which will be used for performance evaluation.

EXAMPLE 10
Perfluoroalkyl-10-undecylenylamides from Polyethyleneimine (PEI)

10a) Reaction of PEI with 10-undecenoic Acid

Into a 300 ml three-necked round bottom flask are placed 80.0 g undecenoic acid (0.434 mol) and 0.7 g phosphoric acid (85%, 6.0 mmol). At a starting temperature of 115° C., 43.4 g of polyethyleneimine (0.0543 mol having an avg. M$_w$ of 800, Lupasol FG from BASF) is slowly added to the acid with stirring while the temperature gradually increases to 158° C. Water begins to collect into a pre-weighed Dean-Stark trap fitted with dry ice condenser. The temperature is increased to 198° C. and is held there for 2 hours, at which time GC shows 1% of unreacted undecenoic acid using an external standard. A viscous, amber liquid is obtained (122.4 g, 98.7%).

10b) Reaction with Acetic Anhydride

Acetic anhydride (1.4 g, 14.1 mmol) is added the intermediate of Example 10a (10.0 g, 4.69 mmol) at 90° C. with stirring. A 14° C. exotherm is noted and the mixture becomes viscous. After one hour of stirring at 100° C., the product is isolated for further reactions.

10c) Reaction with R$_F$-iodide and Emulsification

Following the procedure outlined In Example 2, 21.6 g (0.035 mol) perfluoroalkyl iodide are added to the product of Example 10b. The fluorochemical product is isolated to give to give 29.1 g of a tan wax which is homogenized in the following manner: 20 g of the fluorochemical are dissolved at 70–74° C. into 60.4 g water, 7.0 g dipropylene glycol, 1.0 g acetic acid and 0.9 g Brij 98. The mixture is rapidly stirred for 1.5 hours and then passed three times through a high-pressure homogenizer to give a stable emulsion that will be used for performance evaluation.

EXAMPLE 11
Synthesis of Perfluoroalkyl-10-undecylenylamides/Succinamides from Polyethyleneimine A mixture of 2.4 g (23.9 mmol) succinic anhydride and 10.2 g (4.79 mmol) of the product of Example 9a is stirred at 120° C. for 3 hours to give an amber, viscous material in quantitative yield. GC analysis using an external standard indicates less than 1% of succinic anhydride is unreacted. Following the procedure outlined in Example 2, 21.7 g (0.036 mol) perfluoroalkyl iodide are added to this product. The fluorochemical product is isolated to give 30 g of an amber solid which is dispersed into water in the following manner: with rapid stirring at 60° C., 23.5 g of the fluorochemical is slowly added to a solution of 70.4 g water, 0.59 g Brij 35, 0.2 g Brij 98, and 1.7 g ammonium hydroxide (20%). After one hour, a creamy, stable dispersion is obtained which is used for performance evaluation.

EXAMPLE 12
N,N'-Bis(2-(11-perfluoroalkyl-10-undecylenamido)ethyl) ethylene Disuccinamide 12a) Synthesis of Undecenoic Acid Diamide with Triethylenetetramine 25.3 g (0.137 mol) of 10-undecenoic acid and 10.04 g (0.069 mol) triethylenetetramine are added to a 100 ml three-necked, round-bottom flask equipped with stirrer, condenser and nitrogen sparge inlet, and heated to 150° C. while stirring. After stirring overnight at 150° C., gas chromatography shows <1% 10-undecenoic acid left. 30.8 g (a 94% yield) of a light tan solid is obtained.

12b) Synthesis of R$_F$-undecenoic Acid Diamide-disuccinamide 11.69 g (0.023 mol) of the diamide from Example 12a are added to a 100 ml three-necked, round-bottom flask equipped with stirrer, condenser and nitrogen sparge inlet, and heated to 70° C. while stirring. Then 4.90 g (0.049 mol) succinic anhydride are added over 10 minutes. After 1 hour an additional 1.32 g (0.013 mol) succinic anhydride are added. After 2 hours 26.03 g (0.0438 mol) R$_F$I, 11.15 g n-propanol, 33.44 g water and 0.86 g sodium metabisulfite are added, followed by 0.50 g AIBN. The flask contents are stirred at 70° C. for 5 hours. An opaque light brown paste is obtained. GC analysis on a 30 m×0.53 mm SPB-5 polysiloxane column shows R$_F$I remaining to be <3% of the original charge. 13.5 g (0.169 mol) of a 50% sodium hydroxide solution is slowly charged to the stirred paste and the temperature is raised to 83° C. After 4 hours, iodide titration shows iodine elimination to be complete.

The flask contents are acidified with glacial acetic acid to a pH of 4. The top aqueous layer is removed and the organic layer is washed two times with 35 ml water at 65° C. to remove sodium iodide. The remaining paste is allowed to cool. The remaining aqueous layer is decanted. The solid is stripped of solvents under vacuum at 80° C. overnight and 31.1 g of a brown waxy material is obtained.

EXAMPLE 13
N,N'-Bis(2-(11-perfluoroalkyl-10-undecylenamido)ethyl) ethylene Diacetamide 9.16 g (0.020 mol) of the diamide from Example 12a) are added to a 100 ml three-necked, round-bottom flask equipped with stirrer, condenser and nitrogen sparge inlet, and heated to 100° C. while stirring. Then 4.32 g (0.042 mol) acidic anhydride are added over 10 minutes. After 1 hour 21.16 g (0.0356 mol) $R_FI$, 8.35 g n-propanol, 20.81 g water and 0.71 g sodium metabisulfite are added, followed by 0.50 g AIBN. The contents are stirred at 70° C. for 5 hours. An opaque light brown paste is obtained. GC analysis on a 30 m×0.53 mm SPB-5 polysiloxane column shows $R_FI$ remaining to be <2% of the original charge. To the stirred paste 12.0 g (0.15 mol) of a 50% sodium hydroxide solution is slowly charged and the temperature is raised to 80° C. After 5 hours, iodide titration shows iodine elimination to be complete.

The contents are allowed to settle and cool to 65° C. The top aqueous layer is removed and 8.0 g toluene is charged to aid in washing. The organic layer is washed once with 35 ml water at 65° C. The paste is stripped of solvents under vacuum at 80° C. overnight and 24.1 g of a tan waxy material is obtained.

EXAMPLE 14

N,N'-Bis(2-(11-perfluoroalkyl-10-undecylenamido)ethyl) ethylene Monoacetamide 9.27 g (0.020 mol) of the diamide from Example 12a) are added to a 100 ml three-necked, round-bottom flask equipped with stirrer, condenser and nitrogen sparge inlet, and heated to 100° C. while stirring. Then 2.19 g (0.021 mol) acidic anhydride are added over 10 minutes. After 1 hour 21.37 g (0.0353 mol) $R_FI$, 8.10 g n-propanol, 20.69 g water and 0.50 g sodium metabisulfite are added, followed by 0.66 g AIBN. The contents are stirred at 70° C. for 5 hours. An opaque light brown paste is obtained. GC analysis on a 30 m×0.53 mm SPB-5 polysiloxane column shows $R_FI$ remaining to be <2% of the original charge. To the stirred paste 8.0 g (0.10 mol) of a 50% sodium hydroxide solution is slowly charged and the temperature is raised to 80° C. After 5 hours, titration shows iodine elimination to be complete.

The contents are allowed to settle and cool to 65° C. The top aqueous layer is removed and 8.0 g toluene is charged to aid further washes. The organic layer is washed once with 30 ml of water at 65° C. The paste is stripped of solvents under vacuum at 80° C. overnight and 23.2 g of a tan waxy material is obtained.

EXAMPLE 15

N,N'-Bis(2-(11-perfluoroalkyl-10-undecylenamido)ethyl) ethylene Diamine 11.43 g (0.025 mol) of the diamide from Example 12a) are added to a 100 ml three-necked, round-bottom flask equipped with stirrer, condenser and nitrogen sparge inlet, and heated to 70° C. while stirring. Then 26.36 g (0.0443 mol) $R_FI$, 10.02 g n-propanol, 25.61 g water and 0.58 g sodium metabisulfite are added, followed by 0.78 g AIBN. The contents are stirred at 70° C. for 5 hours. An opaque dark brown paste is obtained. GC analysis on a 30 m×0.53 mm SPB-5 polysiloxane column shows $R_FI$ remaining to be <0.5% of the original charge. To the stirred paste 4.8 g (0.06 mol) of a 50% sodium hydroxide solution is slowly charged and the temperature is raised to 80° C. After 5 hours, titration shows iodine elimination to be complete.

The contents are allowed to settle and cool to 65° C. The top aqueous layer is removed and the organic layer is washed once with 40 ml water. Then 8.0 g toluene is charged to aid further washes. The organic layer is washed once with 40 ml water at 65° C. The paste is stripped of solvents under vacuum at 80° C. overnight and 31.1 g of a dark brown soft sticky material is obtained.

EXAMPLE 16

N,N'-Bis-2-(11-perfluoroalkyl-10-undecylenamidoethyl) ethylene-N,N'-carboxymethyl 6.92 g (0.015 mol) of the diamide from Example 12a) are added to a 100 ml three-necked, round-bottom flask equipped with stirrer, condenser and nitrogen sparge inlet and heated to 70° C while stirring. Then 3.72 g (0.032 mol) sodium chloroacetate are added over 10 minutes. After 5 hours 15.97 g (0.0269 mol) $R_FI$, 7.28 g n-propanol, 13.56 g water and 0.54 g sodium metabisulfite are added, followed by 0.65 g AIBN. The contents are stirred at 70° C for 3.5 hours. An opaque light brown paste is obtained. GC analysis on a 30 m×0.53 mm SPB-5 polysiloxane column shows $R_FI$ remaining to be <4% of the original charge. To the stirred paste 5.76 g (0.072 mol) of a 50% sodium hydroxide solution is slowly charged and the temperature is raised to 80° C. After 5 hours, titration shows iodide elimination to be complete.

The mixture is allowed to settle and cool to 65° C. The top aqueous layer is removed and 7.0 g toluene is charged to aid further washes. The organic layer is washed three times with 35 ml water at 65° C. The paste is stripped of solvents under vacuum at 80° C. overnight and 20.2 g (87% yield) of a soft orange-brown material is obtained. The fluorochemical product is dispersed into water in the following manner: to a rapidly stirred 63° C. solution of 82 g water, 0.5 g Brij 35 [polyoxyethylene(23) lauryl ether], 0.2 g Brij 98 [polyoxyethylene(20) oleyl ether], both from Aldrich Chem., and 1.0 g ammonium hydroxide (20%) are slowly added 16.0 g of the fluorochemical. After 1.5 hours, a creamy, off-white dispersion is obtained which can be used for performance evaluation.

EXAMPLE 17

Polyurea from N,N'-bis(3-(11-perfluoroalkyl-10-undecylenamido)propyl)ethylenediamine and Diisocyanate 11.12 g (0.0213 mol) of the diamide-diamine from Example 1 are added to a 100 ml three-necked, round-bottom flask equipped with stirrer, condenser and nitrogen sparge inlet, and heated to 105° C. while stirring. Then 3.44 g (0.016 mol) 3,3,4(3,4,4)-trimethyl-1,6-diisocyanato hexane (TMDI) are added over 10 minutes. The contents become dark and viscous. After 1 hour 0.71 g (0.007 mol) acetic anhydride are added to acetylate the residual amine groups. After 1 hour 25.37 g (0.0427 mol) $R_FI$, 10.16 g n-propanol, 25.98 g water and 0.62 g sodium meta-bisulfite are added, followed by 0.75 g AIBN. The contents are stirred at 80° C. for 5 hours. An opaque brown paste is obtained. GC analysis on a 30 m×0.53 mm SPB-5 polysiloxane column shows $R_FI$ remaining to be <0.5% of the original charge. To the stirred paste 8.64 g (0.11 mol) of a 50% sodium hydroxide solution is slowly charged. After 5 hours, titration shows iodine elimination to be complete.

The contents are allowed to settle and cool to 65° C. The top aqueous layer is removed and 2.0 g toluene is charged to aid further washes. The organic layer is washed two times with 18 ml water at 65° C. The paste is stripped of solvents under vacuum at 80° C. overnight and 29.48 g of a tan waxy material is obtained.

The product is dispersed into water in the following manner: to a rapidly stirred 63° C. solution of 82 g water, 0.5 g Brij 35 [polyoxyethylene(23) lauryl ether], 0.2 g Brij 98 [polyoxyethylene-(20) oleyl ether], both from Aldrich Chem., and 1.0 g ammonium hydroxide (20%) are slowly added 16.0 g of the fluorochemical. After 1.5 hours, a creamy, off-white dispersion is obtained which can be used for performance evaluation.

EXAMPLE 18
Synthesis of Oligo-$R_F$-amide:
Reaction of di-$R_F$-diamine with 1,2.4.5-benzenetetracarboxylic Dianhydride To a 100 ml three neck flask fitted with a mechanical stirrer, condenser and nitrogen sparge inlet 10 g (6.9 mmoles) of the $R_F$-diamide from Example 2 and 10 g of 1-methyl-2-pyrrolidinone are added. The mixture is heated to 50° C. and 1.43 g (6.6 mmoles) of 1,2,4,5-benzenetetracarboxylic dianhydride is added. The reaction is heated at 52° C. for 3 hours. To the reaction mixture 0.4 g of ammonium hydroxide in 35 g water is added and the mixture is stirred at 75° C. for 1 hour, resulting in a brown solution having a pH of 9 and 20% solids.

EXAMPLE 19
Diethylenetriamine, N,N"-bis-4-$R_F$-3-pentenamido,-N'-acetamide

19a) Reaction of Diethylenetriamine with 4-pentenoic Acid

A 100 ml three-neck flask fitted with a mechanical stirrer and condenser is charged with 15.5 g (0.15 moles) of diethylenetriamine; 30 g (0.3 moles) 4-pentenoic acid are slowly added while the reaction temperature is increased to 180° C. It is held at this temperature for 5 hours, after which time 4.8 g (90% of the theoretical value) of water has been collected. The reaction is stopped at this stage and 41 g of the diamido-amine product is collected as a tan solid.

19b) Reaction with Acetic Anhydride

In 10 g methyl ethyl ketone that had been dried over molecular sieves are dissolved 10 g of diamidoamine from Example 19a. To this solution are slowly added 14 g of acetic anhydride and the reaction mixture is heated at 65° C. for 30 minutes, after which time acetylation is complete, as determined by titration. Then 10 g isopropanol are added and the mixture is stirred for 15 more minutes at 65° C., forming a clear solution. The product is isolated by drying at high vacuum, yielding a brown solid.

19c) Reaction with $R_F$-iodide

A 100 ml three neck flask fitted with a mechanical stirrer, condenser and nitrogen sparge inlet is charged with 10.0 g (0.032 moles) of the diamidoamine of Example 19b. Then 3.5 g 1-propanol and 6 g water are added, followed by 35.0 g (0.057 moles) of $R_F$I (DuPont's Zonyl Tel A-N). The mixture is heated and stirred at 76° C. while 0.6 g (3.2 mmoles) of sodium metabisulfite and 0.25 g (2.1 mmoles) of VAZO-67 are added. Stirring is continued at 75° C. while reaction's progress is followed by gas chromatography. After 4 hours 8% of the $R_F$I is left unreacted. Then 8.0 g of 50% NaOH are added and the mixture is stirred at 70° C. Iodide titration shows that dehydrohalogenation is complete after 4 hours. The reaction mixture is further diluted with enough water to result in a brown aqueous 16% solids dispersion.

EXAMPLE 20
Synthesis of di-$R_F$-dicarboxylic Acid Amides from tri- and di-amine and Tetrahydrophthalic Anhydride 20a) Reaction of cis-1,2,3,6-tetrahydrophthalic Anhydride (THPA) with Diethylenetriamine A three neck round bottom flask is charged with 10.0 g (0.066 moles) THPA, 10.0 g 1-methyl-2-pyrrolidinone and 15.0 g of toluene. The contents are cooled to 10° C. and 3.2 g (0.031 moles) of diethylenetriamine are slowly added. The reaction mixture is stirred for 30 minutes at 10° C. and then at room temperature for 4 hours. The product is precipitated into toluene and dried to a brown, gummy solid.

20b) Addition of $R_F$I:

6.0 g (0.0147 moles) of the reaction product of Example 20a are charged to a 100 ml three neck flask fitted with mechanical stirrer, condenser and nitrogen sparge inlet. Then 6.0 g of water and 1.2 g of NaOH are added. The contents of the flask are stirred for 30 minutes, followed by addition of 12.0 g of 2-propanol and 15.8 g (0.026 moles) of $R_F$I (DuPont's Zonyl Tel A-N). The mixture is stirred at 72° C. and a solution of 0.3 g (1.95 mmoles) Rongalite in 0.7 g of water is added. The progress of the reaction is followed by gas chromatography. The contents are stirred at 75° C. for 4 hours, after which time no $R_F$I is detected. Then 2.0 g of 50% NaOH solution are added and the mixture is stirred at 72° C. for 6 hours, after which time iodide titration shows that dehydrohalogenation is complete. The mixture is neutralized with dilute HCl and 2-propanol is removed on a rotary evaporator. The precipitated product is washed with water and dried at high vacuum to give 19 g of a yellow solid which is dispersed in aqueous ammonium hydroxide, resulting in a brown dispersion having a pH of 10 and 25% solids.

EXAMPLE 21
21a) Reaction of cis-1,2,3,6-tetrahydrophthalic Anhydride (THPA) with Ethylenediamine A three neck round bottom flask is charged with 10.0 g (0.066 moles) THPA, 10.0 g 1-methyl-2-pyrrolidinone and 10.0 g of toluene. The contents are cooled to 10° C. and 1.9 g (0.032 moles) of ethylenediamine are slowly added. The reaction mixture is stirred for 30 minutes at 10° C. and then at room temperature for 4 hours. The product is precipitated into toluene and dried to give 10.5 g of a white powder.

21 b) Addition of $R_F$I:

5.0 g (0.014 moles) of the reaction product of Example 21a are charged to a 100 ml three neck flask fitted with a mechanical stirrer, condenser and nitrogen sparge inlet, 10.0 g of water and 2.3 g of NaOH are added and the contents of the flask are stirred for 30 minutes, followed by addition of 10.0 g of 2-propanol and 16.0 g (0.027 moles) of $R_F$I (DuPont's Zonyl Tel AN). The mixture is stirred at 72° C. To the reaction mixture a solution of 0.3 g (1.95 mmoles) Rongalite in 0.7 g water is added. The progress of the reaction is followed by gas chromatography. The contents are stirred at 75° C. for 4 hours Then 2.0 g of 50% NaOH solution are added and the mixture is stirred at 75° C. After 6 hours iodide titration shows that dehydrohalogenation is complete. The mixture is neutralized with dilute HCl and the 2-propanol is removed on a rotary evaporator. The precipitated product is washed with water and dried at high vacuum to give 19 g of a yellow solid, which is dispersed in aqueous ammonium hydroxide, resulting in a brown dispersion having a pH of 10 and 24% solids.

EXAMPLE 22
Synthesis of Diethylenetriamine-N,N"-bis-11-$R_F$-10-undecylenylamide-N'-acetamide 22a) Diethylenetriamine-N,N"-bis-10-undecylenylamide-N'-acetamide 6.36 g (0.0624 mol) acetic anhydride are added to the 25 g (0.0594 mol amine) of the product of Example 5a) at 90° C. The melt is stirred at 90° C. for 1.5 hours, then gradually heated to 112° C. and held there for an additional hour. GC analysis (using an external standard) indicates complete reaction of the anhydride.

22b) $R_F$-I Addition and Emulsification.

Following the procedure outlined in Example 2, 72.4 g (0.119 mol) perfluoroalkyl iodide is added to the product of Example 22a. The fluorochemical product is isolated to give 79 g of an amber solid that is dispersed into water in the following manner: to a rapidly stirred 63° C. solution of 82 g water, 0.5 g Brij 35, 0.2 g Brij 98 and 1.0 g ammonium hydroxide (20%) are added 16.0 g of the fluorochemical.

After 1.5 hours, a creamy, off-white dispersion is obtained which can be used for performance evaluation.

Examples 23–24 show the performance of the novel $R_F$-compounds as internal and external paper sizes.

EXAMPLE 23

Performance of the New Compounds as External Paper Sizes.

Example Preparation and Testing:

The required amounts of 2% solutions of the test compounds in distilled water are dissolved in enough aqueous ammonia to achieve complete neutralization of the acid groups; the pH of the resulting solutions or dispersions is 9 to 9.5. Samples of the fluorochemicals are then diluted to the test application levels with distilled water.

The neutralized test solutions are added to a 4% aqueous solution of paper maker's starch (Stayco M, oxidized starch, from Staley Corp.) and then applied to unsized paper by padding (paper dipped through starch solution, and passed through single nip rollers). The resulting sheets are dried at ambient conditions for 15 minutes, then 3 minutes at 200° F. (93° C.) in an "Emerson Speed Drier" (heated metal plate with canvas cover).

Oil Kit Test:

The oil repellency of the surface is determined by using the TAPPI UM 557 OIL KIT TEST, which consists of determining with which of twelve castor oil-heptanetoluene mixtures having decreasing surface tension penetration occurs within 15 seconds; ratings go from 1, lowest, to 12.

Ralston-Purina (RP2) Test:

Grease resistance is determined with the Ralston-Purina test for pet food materials; RP-2 Test, Ralston-Purina Company, Packaging Reference Manual Volume 06—Test Methods.—In summary: cross-wise creased test papers are placed over a grid sheet imprinted with 100 squares. Five grams of sand are placed in the center of the crease. A mixture of synthetic oil and a dye for visualization is pipetted onto the sand and the samples are maintained at 60° C. for 24 hours. Ratings are determined by the percentage of stained grid segments, using at least two samples.

Turpentine Test, according to TAPPI T454om-94, is a preliminary test to determine rates at which oil or grease can be expected to penetrate paper.

Cobb Size Test

Water resistance is determined using the Cobb Sizing test as described in TAPPI T 441 om-90.

TABLE 1

Performance of new compounds as external paper sizes

| Compound of Ex. No. | F, % on Paper | Oil Kit | RP-2, % | Turp., Sec. | Cobb 2 min. |
|---|---|---|---|---|---|
| 2 | .05 | 7 | .25 | 180 | 64 |
|  | .07 | 10 | 0 | 1800+ | 59 |
|  | .09 | 12 | 0 | 1800+ | 72 |
| 5 | .06 | 7 | 0 | 30 | 79 |
|  | .09 | 9 | 0 | 1800+ | 75 |
|  | .12 | 11 | 0 | 1800+ | 80 |
| 6 | .06 | 7 | .5 | 30 | 86 |
|  | .07 | 8 | 0 | 90 | 86 |
|  | .10 | 8 | 0 | 100 | 75 |
| 10 | .06 | 9 | 0 | 1800+ | 62 |
|  | .08 | 11 | 0 | 1800+ | 65 |
|  | .11 | 12 | 0 | 1800+ | 61 |
| 12 | .06 | 8 | 0 | 1800+ | 56 |
|  | .08 | 12 | 0 | 1800+ | 40 |
|  | .11 | 12 | 0 | 1800+ | 26 |
| 14 | .05 | 7 | 0 | 1800+ | 72 |
|  | .08 | 12 | 0 | 1800+ | 65 |
|  | .10 | 12 | 0 | 1800+ | 64 |
| 16 | .06 | 7 | 0 | 1800+ | 68 |
|  | .07 | 10 | 0 | 1800+ | 63 |
|  | .10 | 12 | 0 | 1800+ | 56 |
| 18 | .06 | 6 | 0 | 60 | 71 |
|  | .08 | 8 | 0 | 1800+ | 69 |
|  | .11 | 10 | 0 | 1800+ | 64 |
| 22 | .04 | 7 | 15 | 30 | 76 |
|  | .06 | 8 | 1 | 600 | 79 |
|  | .08 | 10 | 0 | 1800+ | 72 |

EXAMPLE 24

Performance of New Compounds as Internal Paper Sizes

Example Preparation and Testing:

Six grams of dry recycled pulp consisting of 70% hardwood and 30% softwood are diluted in 289 ml distilled water and thoroughly dispersed in a blender. To this pulp slurry is added the required amount of a 1% solution of the test compound in distilled water and mixed in for 5 minutes. Then 6 ml of a 1% aqueous solution of cooked cationic starch are added and mixed together for an additional 5 minutes. To this mixture 24 ml of a 50% (on solids) dilution of a water-repellent adjuvant AKD (alkyl-ketene-dimer; Hercon-76, from Nalco Chem. Corp.) are added and mixed in for another 10 minutes. The resulting slurry is diluted with an additional 500 ml of distilled water and mixed again. This mixture is then poured over a 100-mesh wire screen, with a vacuum applied from below that pulls the water from the pulp mixture to form a sheet on the screen. The wet sheet is removed from the screen and dried between another screen and a hard surface at a pressure of approximately 0.4 lb./in$^2$ at 110° C. for 1½ hours.

Hot-oil Test for Molded Paper (Internal Size):

One ml of hot (110° C.) corn oil is placed on paper and the time is recorded for penetration to occur (20 minutes maximum). Paper made in the same manner, including the cationic starch and water-repellent adjuvant, but without a fluorochemical, demonstrates an oil kit number of <1 and holds the hot corn oil for less than one minute (begins to penetrate as soon as applied). The amount of oil absorbed is determined gravimetrically by weighing the paper before and after the hot-oil test, and after the surface oil has been removed.

Hot-water Test for Molded Paper (Internal Size):

One ml of a hot (83° C.) 5% lactic acid solution is placed on the paper plate, and hold-out time and absorption are measured the same way as in the hot-oil test. The results are shown in the following table.

TABLE 2

Performance of new compounds as internal paper sizes

| Compound of Ex. No. | % F | Hot Oil min./% abs. | Hot 2% Saline min./% abs. initial | After 24 hrs. |
|---|---|---|---|---|
| 7 | 0.07 | 3/26 | >20 | >20/6 |
|  | 0.13 | >20/0 | 20 | 20/28 |

TABLE 2-continued

Performance of new compounds as internal paper sizes

| Compound of Ex. No. | % F | Hot Oil min./% abs. | Hot 2% Saline min./% abs. initial | After 24 hrs. |
|---|---|---|---|---|
| 16 | 0.09 | >20/1 | >20 | >20/6 |
|  | 0.17 | >20/0 | 20 | >20/11 |
| 17 | 0.07 | >20/0 | 20 | 20/11 |
|  | 0.15 | >20/0 | 20 | 20/12 |
| 18 | 0.07 | >20/2 | 20 | 20/10 |
|  | 0.14 | >20/0 | 2 | 2/50 |
| 20 | 0.13 | >20/0 | 20 | 20/18 |
|  | 0.26 | >20/0 | 20 | >20/5 |
| 21 | 0.12 | >20/0 | 20 | 20/24 |
|  | 0.24 | >20/0 | 20 | >20/9 |
| 22 | 0.08 | >20/0 | >20 | >20/6 |
|  | 0.16 | >20/0 | 20 | 20/21 |

What is claimed is:

1. A mono-, di- or polyamide compound of the formula

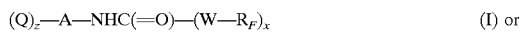 (I) or

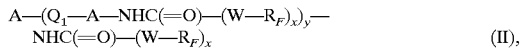 (II), wherein

A is the hydrocarbon residue of an aliphatic, cycloaliphatic or aromatic mono-, di- or polyamine of 60 to 2000 molecular weight, which is optionally substituted by hydroxy- and/or carboxy groups and whose carbon chain is optionally interrupted by one or more ether, amide or amino groups, which amino groups are optionally substituted by substituents of the formula —Q— or —$Q_1$—, in which Q is a monovalent radical connected to a nitrogen atom of (A) and is derived from an acid, acid chloride or lower alkyl ester, an anhydride, a halogenated carboxylic acid, an alkyl or alkenyl halide, an oxirane compound or chloroacetamide, and which is optionally substituted by one or more hydroxy-, tert. amino or carboxy groups, or is optionally interrupted by one or more ether or thioether linkages, and optionally contains one or more unsaturated groups and can be substituted by an $R_F$ group, or is —P(=O)(OH)$_2$; —SO$_3$H, or —C(=O)—NH$_2$;

$Q_1$ is a difunctional linking group attached to the nitrogen atoms of two A groups and is derived from a diacid, diacid chloride or -lower alkyl ester; a dianhydride, a diisocyanate, epichlorohydrin, or is —C(=O)—, or is a trifunctional group derived from cyanuric acid;

each $R_F$ is independently a monovalent perfluorinated alkyl or alkenyl, linear or branched organic radical having four to twenty fully fluorinated carbon atoms;

W is —(CH$_2$)$_p$CH=CH— in which p is 1 to 20, or is a $C_6$–$C_{10}$cycloaliphatic hydrocarbyl group connecting an $R_F$ group to an amide carbonyl;

z is zero to 50, y is zero to 50 and x is 1 to 10.

2. A compound of the formula (I) or (II) according to claim 1, wherein W is of the formula —(CH$_2$)$_p$CH—CH— in which p is 5 to 12 and is derived from a terminally unsaturated alkenoic acid, or is derived from tetrahydrophthalic anhydride or (methyl)-norbornene anhydride; and $R_F$ is saturated and contains 4–14 carbon atoms, is fully fluorinated and contains at least one terminal perfluoromethyl group.

3. A compound of the formula (I) or (II) according to claim 1, wherein W is of the formula —(CH$_2$)$_p$CH=CH— in which p is 8, and $R_F$ is saturated and contains 6–12 fully fluorinated carbon atoms.

4. A compound of the formula (I) or (II) according to claim 1, wherein A is the hydrocarbon residue of an optionally substituted and/or interrupted monoamine.

5. A compound according to claim 4, wherein A is the hydrocarbon residue of glycine, p-aminosulfonic acid, taurine, 2-hydroxyethanolamine or is a tert. amino-substituted residue of the formula —(CH$_2$)$_j$—N—(R$_1$)$_2$ wherein j is 2 to 6 and each R$_1$ is C$_1$-C$_4$alkyl.

6. A compound of the formula (II) according to claim 5, wherein A is a tert. amino-substituted amine residue of the formula —(CH$_2$)$_j$—N—(R$_1$)$_2$ wherein j is 2 to 6 and each R$_1$ is independently C$_1$-C$_4$alkyl, W is of the formula —(CH$_2$)$_p$CH=CH— in which p is 8, and $R_F$ is saturated and contains 6–12 fully fluorinated carbon atoms.

7. A compound of the formula (I) or (II) according to claim 1, wherein A is the hydrocarbon residue of an optionally substituted and/or interrupted diamine.

8. A compound according to claim 7, wherein A is the hydrocarbon residue of a diamine of the formula H$_2$N—(CH$_2$)$_n$—NH$_2$ wherein n is 2–6, or is p-phenylenediamine, lysine, or a diamine of the formula H$_2$N—(CH$_2$)$_3$—O—(CH$_2$—CH$_2$—O)$_m$—(CH$_2$—CHCH$_3$—O)$_l$—(CH$_2$)$_3$—NH$_2$, wherein m and l are independently 0 to 50 and m plus l is ≧1.

9. A compound of the formula (I) or (II) according to claim 1, wherein A is the hydrocarbon residue of an optionally substituted and/or interrupted polyamine.

10. A compound according to claim 9, wherein A is the hydrocarbon residue of a polyalkylene-amine of the formula H$_2$N—(CH$_2$CHR—NH)$_n$—CH$_2$CHR—NH$_2$, wherein n is 1 to 5 and R is hydrogen or methyl, or aminoethylpiperazine, iminobispropylamine or N,N'-bis(3-aminopropyl)-ethylenediamine, or is a polyethyleneimine of molecular weight 200 to 2,000 or polylysine.

11. A compound of the formula (I) or (II) according to claim 1, wherein A is the optionally substituted and/or interrupted hydrocarbon residue of a polyethyleneimine of molecular weight 200 to 1,000, diethylenetriamine, triethylenetetramine, N,N'-bis(3-aminopropyl)ethylenediamine, lysine or polylysine.

12. A compound of the formula (I) or (II) according to claim 1, wherein Q is of formula —C(=O)CH$_3$; —(CH$_2$)$_{1-3}$COOH; —C(=O)—CR=CH$_2$, wherein R is hydrogen or methyl; —CH$_2$CH=CH$_2$; —CH$_2$CH(OH)CH$_2$—O—CH$_2$CH=CH$_2$; —CH$_2$—CH=CH—$R_F$ or —CH$_2$CH(OH)CH$_2$—O—CH$_2$—CH=CH—$R_F$, where $R_F$ is as defined in claim 1; —C(=O)—(CH$_2$)$_2$—COOH; —C(=O)—CH=CH—COOH; —C(=O)—C(=CH$_2$)—CH$_2$—COOH; —(=O)—CH$_2$—C(=CH$_2$)—COOH; —C(=O)—(C$_6$H$_8$)—COOH; —C(=O)—(C$_7$H$_8$)—COOH; —C(=O)—(C$_8$H$_{10}$)—COOH; —C(=O)—(CH$_2$)$_8$CH=CH$_2$; —CH$_2$—CHOH—CH$_2$—O—(CH$_2$CHR—O)$_m$—R$_2$, where m is 1 to 50 and R$_2$ is hydrogen or C$_1$-C$_{12}$alkyl; —P(=O)(OH)$_2$; —SO$_3$H, or —CH$_2$CH$_2$N(CH$_3$)$_2$.

13. A compound according to claim 12, wherein Q is of the formula —C(=O)CH$_3$; —C(=O)—CH=CH$_2$; —CH$_2$—COOH; —C(=O)—(CH$_2$)$_2$—COOH or —C(=O)—(C$_6$H$_8$)—COOH.

14. A compound of the formula (I) or (II) according to claim 1, wherein Q, is of formula —(C=O)—HN—Z—

NHC(=O)—, wherein Z is the diradical hydrocarbon residue of p or m-toluene diisocyanate, isophorone diisocyanate, 3,3,4(3,4,4)-trimethylhexane-1,6-diisocyanate or hexane-1, 6-diisocyanate; —C(=O)—; —CH$_2$—CHOH—CH$_2$— or —CH$_2$—CHOH—CH$_2$—O—(CH$_2$CH$_2$—O)$_m$— (CH$_2$CHCH$_3$—O)$_l$—CH$_2$—CHOH—CH$_2$—, wherein m and l are independently 0 to 50 and m plus l is ≥1; —C(=O)—C$_6$H$_4$(—COOH)$_2$—C(=O)—; or —C(=O)—CH$_2$C(=CH$_2$)—C(=O)— or —C(=O)—D—C(=O)—, wherein D is the hydrocarbon residue of an aliphatic or aromatic dicarboxylic acid having from 2 to 10 carbon atoms.

15. A compound according to claim 14, wherein $Q_1$ is of the formula: —CH$_2$—CHOH—CH$_2$—; —C(=O)—C$_6$H$_4$(—COOH)$_2$—C(=O)—; —C(=O)—CH$_2$CH$_2$—C(=O)— or —C(=O)HN—Z—NHC(=O)— wherein Z is the diradical residue of p or m-toluene diisocyanate, isophorone diisocyanate, 3,3,4(3,4,4)-trimethylhexane-1, 6diisocyanate or hexane-1,6-diisocyanate.

16. A compound according to claim 1, which is of the formula

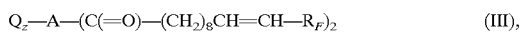

$$Q_z—A—(C(=O)—(CH_2)_8CH=CH—R_F)_2 \qquad (III),$$

wherein

A is derived from diethylenetriamine, triethylenetetramine or N,N'-bis(3-aminopropyl)ethylene-diamine, Q is —C(=O)CH$_3$; —C(=O)—CH=CH$_2$; —CH$_2$—COOH; —C(=O)—(CH$_2$)$_2$—COOH or —C(=O)—(C$_6$H$_8$)—COOH, z is 1 or 2, and each $R_F$ is independently a monovalent perfluorinated linear alkyl radical having 6 to 14 fully fluorinated carbon atoms.

17. A compound according to claim 1, which is of the formula

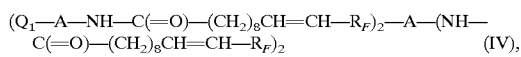

$$(Q_1—A—NH—C(=O)—(CH_2)_8CH=CH—R_F)_2—A—(NH—C(=O)—(CH_2)_8CH=CH—R_F)_2 \qquad (IV),$$

wherein A is derived from diethylenetriamine and $Q_1$ is a difunctional radical of the formula —CH$_2$—CHOH—CH$_2$—; —C(=O)—CH$_2$CH$_2$—C(=O)—; —C(=O)—; —C(=O)—C$_6$H$_4$(—COOH)$_2$—C(=O)—, or —C(=O)—NH—Z—NH—C(=O)—, wherein Z is the diradical hydrocarbon residue of p- or m-toluene diisocyanate, isophorone diisocyanate, 3,3,4(3,4,4)-trimethylhexane-1,6-diisocyanate or hexane-1,6-diisocyanate, and each $R_F$ is independently a monovalent perfluorinated linear alkyl radical having 6 to 14 fully fluorinated carbon atoms.

18. A compound according to claim 17, which is of the formula

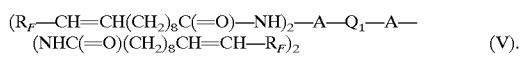

$$(R_F—CH=CH(CH_2)_8C(=O)—NH)_2—A—Q_1—A—(NHC(=O)(CH_2)_8CH=CH—R_F)_2 \qquad (V).$$

19. A compound according to claim 1, which is of the formula

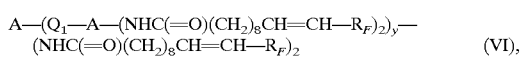

$$A—(Q_1—A—(NHC(=O)(CH_2)_8CH=CH—R_F)_2)_y—(NHC(=O)(CH_2)_8CH=CH—R_F)_2 \qquad (VI),$$

wherein y is 2 to 50, A is derived from triethylenetetramine or N'N-bis(3-aminopropyl)ethylenediamine and $Q_1$ is of the formula —CH$_2$—CHOH—CH$_2$—, —C(=O)—CH$_2$CH$_2$—C(=O)—; —C(=O)—, —C(=O)—C$_6$H$_4$(—COOH)$_2$—C(=O)—, or —C(=O)—HN—Z—NH—C(=O)—, wherein Z is the diradical hydrocarbon residue of p- or m-toluene diisocyanate, isophorone diisocyanate, 3,3,4(3,4,4)-trimethylhexane-1,6-diisocyanate or hexane-1,6-diisocyanate.

20. A process for the preparation of a compound of the formula (I) or (II) according to claim 1, which comprises reacting an aliphatic, cycloaliphatic or aromatic mono-, di- or polyamine with an $R_F$-acid, -ester or -anhydride and then reacting any remaining amino groups with an amino-reactive non-fluorinated compound.

21. A process for the preparation of a compound of the formula (I) or (II) according to claim 1, which comprises reacting a linear terminally-unsaturated monocarboxylic acid or its lower alkyl ester, or tetrahydrophthalic anhydride with a polyamine, to form an oligoamide with residual secondary amino groups, reacting any remaining amino groups of this oligoamide with an amino-reactive non-fluorinated compound, and then reacting this ethylenically unsaturated intermediate with an $R_F$-iodide.

22. A process according to claim 21 wherein the linear terminally-unsaturated monocarboxylic acid or its lower alkyl ester is 10-undecenoic acid or its lower alkyl ester.

23. A composition which is an essentially aqueous solution comprising 15 to 50% of a compound of the formula (I) or (II) according to claim 1.

24. A method to impart oil and grease resistance to paper, which comprises incorporating into the paper an amount of a compound of the formula (I) or (II) according to claim 1 that is effective to impart oil and grease resistance.

25. A method to impart oil and grease resistance to paper, which comprises incorporating into the paper an amount of a compound of the formula (I) according to claim 16 that is effective to impart oil and grease resistance.

26. A method to impart oil and grease resistance to a textile material, which comprises treating the textile material with an amount of a compound of the formula (I) or (II) according to claim 1 that is effective to impart oil and grease resistance to the textile material.

27. A method to impart oil and grease resistance to a textile material, which comprises treating the textile material with an amount of a compound of the formula (II) according to claim 17 that is effective to impart oil and grease resistance to the textile material.

28. Textile material or paper or pulp which contains from 0.005 to 0.5% by weight of a compound of the formula (I) or (II) according to claim 1 incorporated therein.

29. Paper or pulp which contains from 0.005 to 0.5% by weight of a compound of the formula (I) according to claim 16 incorporated therein.

30. Textile material or paper or pulp which contains from 0.005 to 0.5% by weight of a compound of the formula (II) according to claim 16 incorporated therein.

* * * * *